United States Patent [19]

Heinrich et al.

[11] 4,230,809
[45] Oct. 28, 1980

[54] PRESSURE-RESISTANT POLYURETHANE-POLYUREA PARTICLES FOR THE ENCAPSULATION OF ACTIVE INGREDIENTS AND PROCESS FOR THEIR MANUFACTURE

[75] Inventors: Rudolf Heinrich, Kelkheim; Heinz Frensch, Frankfurt am Main; Konrad Albrecht, Kelkheim, all of Fed. Rep. of Germany

[73] Assignee: Hoechst Aktiengesellschaft, Frankfurt am Main, Fed. Rep. of Germany

[21] Appl. No.: 971,099

[22] Filed: Dec. 19, 1978

[30] Foreign Application Priority Data

Dec. 21, 1977 [DE] Fed. Rep. of Germany ....... 2757017

[51] Int. Cl.$^2$ .................. C08G 18/14; C08G 18/08
[52] U.S. Cl. .................. 521/65; 260/29.2 TN; 521/51; 521/114; 521/130; 528/48; 528/902; 424/16
[58] Field of Search ............ 528/48, 902; 521/65, 521/114, 130; 260/29.2 TN

[56] References Cited

U.S. PATENT DOCUMENTS

| | | | |
|---|---|---|---|
| 3,402,149 | 9/1968 | Walters | 260/75 |
| 3,577,515 | 5/1971 | Vandegaer | 260/29.2 TN |
| 3,651,182 | 3/1972 | Rosenthal | 264/51 |
| 3,850,880 | 11/1974 | Hakanson et al. | 260/75 NE |
| 3,860,565 | 1/1975 | Barber | 528/902 |
| 3,963,710 | 6/1976 | Aufdermarsh | 528/902 |
| 4,000,218 | 12/1976 | Critchfield et al. | 528/902 |
| 4,032,516 | 6/1977 | McGarr | 260/77.5 AA |
| 4,046,741 | 9/1977 | Scher | 528/68 |

OTHER PUBLICATIONS

DAS 1817316, Watanabe et al., Dec. 18, 1969.
DAS 2043556, Matsukawa et al., Mar. 25, 1971.
DOS 2242910, Kiritani et al., Mar. 15, 1973.
DOS 2251381, Kiritani et al., Apr. 26., 1973.
DOS 2311712, Schnoring et al., Sep. 19, 1974.
DOS 2312059, Scher, Sep. 20, 1973.
DOS 2404538, Schnoring et al., Aug. 7, 1975.
DOS 2557407, Schnoring et al., Jun. 30, 1977.

*Primary Examiner*—H. S. Cockeram
*Attorney, Agent, or Firm*—Curtis, Morris & Safford

[57] ABSTRACT

Pressure-resistant polyurethane-polyurea particles with textured internal mass prepared from a liquid phase immiscible with water and containing organic solvents, isocyanate prepolymers and optionally active substances or mixtures of active substances, the liquid phase being dispersed in an aqueous phase at temperatures of from 0° C. to 95° C., wherein the liquid organic phase contains as isocyanate prepolymer a reaction product of a stoichiometric excess of an aliphatic, aromatic, cycloaliphatic, or araliphatic di- or polyisocyanate with a di- or polyol, the reaction product having a mean molecular weight in the range of from about 300 to 10,000, and an alkyl and/or alkoxyalkyl acetate of the formula

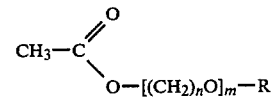

in which m is zero, 1 or 2, n is 1 to 4, and R is ($C_1$–$C_5$)alkyl, and the aqueous phase contains a protective colloid and optionally a surface-active agent.

14 Claims, No Drawings

PRESSURE-RESISTANT POLYURETHANE-POLYUREA PARTICLES FOR THE ENCAPSULATION OF ACTIVE INGREDIENTS AND PROCESS FOR THEIR MANUFACTURE

This invention relates to novel, pressure-resistant polyurethane-polyurea particles with textured internal mass having advantageous utilitarian properties resulting therefrom for the microencapsulation of active substances, especially for plant protection.

In recent years the technique of microencapsulation has gained in importance, since this method makes it possible to enclose substances of different states of aggregation in capsules made of inert material. Many mechanical and chemical processes for the manufacture of capsules have been described and are being used (cf. I. E. Vandegaer "Microcapsulation", Plenum Press, New York-London; 1974). Microcapsules are being used as carrier for many different substances such as inks and dyes, odoriferous substances or flavors, pharmaceutical preparations, chemical reagents and the like, and attempts have been made repeatedly to use plant protecting agents in microcapsules.

It is especially important to encapsulate toxic plant protecting agents with regard to the safety of handling. Another advantage of the encapsulation of active substances is the possibility to combine substances that cannot be blended or are incompatible with one another. The encapsulation of substances with intense smell with a view of reducing olfactory irritation can also be advantageous. A further important advantage of the encapsulation resides in the fact that the active substance can be released in controlled manner over a prolonged period of time (depot effect). By this "slow release" effect the active substance can be better utilized, the number of applications can be diminished and, hence, the total amount of active substance to be applied can be reduced. Due to the better utilization of the active substances, a reduction of the required applications means not only less labor but also a weaker polluting effect on the environment by residues of plant protecting agents. A further result of the controlled release of the active substances is that the crop plants are better protected against phytotoxic damages.

The technique of microencapsulation has not yet gained the appropriate practical importance in plant protection and this is mainly due to the insufficient mechanical stability of the particles for most applications or to difficulties resulting from the presence of phytotoxic monomer residues that have not been completely reacted in the manufacture of the capsules.

It has been proposed to produce polyureas or polyurethanes from di- or polyisocyanates or the prepolymers thereof using di- or polyamines as chain lengthening components and to make use of this reaction for the manufacture of microcapsules.

In DE-AS No. 1,519,853 there is described the manufacture of oil-containing capsules from a low molecular weight hydrophobic phase containing isocyanate groups and a hydrophilic phase containing water, diols or amines. Due to their thin walls, the capsules obtained in this manner do not have a sufficient mechanical stability as carrier for plant protecting agents for practical application. It has, therefore, been proposed, for example in DE-AS No. 1,817,316, to reinforce the walls of the capsules. This multi-stage process is time-consuming and when the capsules obtained in this manner are damaged, the enclosed active substance is released immediately and completely.

DE-AS No. 2,043,556 describes a process for the manufacture of microcapsules wherein the film-forming materials contained in oil droplets migrate to the surface of said oil droplets where they build up a wall material. Similar to the capsules obtained according to the process of DE-OS No. 2,109,335, the capsules obtained in this manner have a poor mechanical stability and are relatively sensitive to pressure.

DE-OS No. 2,242,910 and DE-OS No. 2,251,381 also describe microcapsules which are prepared from isocyanate prepolymers. Both processes use polyamines as chain lengthening components, which have a limited suitability only in plant protection because of their phytotoxicity.

According to DE-OS No. 2,311,712 the reaction product of a di- or polyol with phosgene or a di- or polyisocyanate is reacted with polyamines, polyesters, polyethers, polyacetals or polyols. In this manner capsules likewise having very thin walls are obtained which are relatively sensitive to pressure and which release the active substance contained therein rapidly and completely in the case of damage.

The situation is similar with the process described in DE-OS No. 2,312,059, which yields polyurea capsules having extremely thin walls.

DE-OS No. 2,404,538 relates to a continuous process for the manufacture of a polyurethane/polyurea powder by interfacial polyaddition. The powder particles, which may also enclose other substances, are obtained by spraying a polyisocyanate or a prepolymer into a phase consisting of gaseous di- or polyamine. In this process the interfacial polyaddition takes place in the flying phase of the pulverized isocyanate or isocyanate prepolymer. According to another known process (DE-OS No. 2,557,407) polyurethane/polyurea hollow beads are produced from a polyisocyanate or isocyanate prepolymer by polyaddition with a di- or polyamine in the gaseous phase. In a special variant of this process beads are obtained the shell of which consists of polyurea on the outside and of polyurethane inside.

All microcapsules produced according to the aforesaid known processes are unsuitable for practical use in the field of plant protection because of their insufficient mechanical stability and/or a disturbing content of monomer residues having a phytotoxic action, especially amines.

It is the intention to overcome these disadvantages by the microcapsules prepared by the process of the invention.

It is, therefore, the aim of the present invention to manufacture pressure-resistant, non phytotoxic particles for the encapsulation of active substances, especially for plant protection, which remain substantially undamaged when applied in the field by appropriate means and do not lose their specific utilitarian properties on occasion of a possible mechanical damage, especially the ability to release the active substance slowly and in controlled manner. In the manufacture of the carrier particles the plant protecting agents should be encapsulated in said particles and the dispersion or the powder obtained by drying should be suitable for plant protection without further purification.

With a view to the afore-described problems, the following aspects were of special importance to the invention:

Due to the fact that many di- or polyamines are characterized by a more or less pronounced phytotoxic activity, it was not possible to use the diamines employed in most cases for the wall formation of microcapsules. In their stead the isocyanate component was reacted with water.

To prevent the active substance to be encapsulated from a possible reaction with the isocyanate components required for the formation of the carrier particles, relatively reaction inert isocyanate prepolymers were used.

Suitable isocyanate prepolymers of this type are, for example, reaction products of di- or polyisocyanates with compounds containing a plurality of OH groups, for example di- or polyols. The di- or polyisocyanates are used in an excess so that the reaction products formed still contain a sufficient number of free isocyanate groups which can react like polyisocyanates (cf. R. Vieweg, A. Höchtlen, Kunststoff-Handbuch, volume VII, pages 84 et seq., edited by Carl Hanser, Munich 1966).

It is, therefore, the object of the present invention to provide novel, pressure-resistant polyurethane-polyurea particles with textured internal mass.

It is another object of the invention to provide a process for the manufacture of novel, pressure-resistant polyurethane-polyurea particles with textured internal mass from a liquid phase immiscible with water and containing organic solvents, isocyanate prepolymers and optionally active substances or mixtures of active substances, by dispersion in an aqueous phase with reaction of the isocyanate groups at temperatures of from 0° C. to 95° C., which comprises dispersing a liquid organic phase containing as isocyanate prepolymer a reaction product of a stoichiometric excess of an aliphatic, aromatic, cycloaliphatic, or araliphatic di- or polyisocyanate with a di- or polyol, the reaction product having a mean molecular weight in the range of from about 300 to 10,000, and an alkyl and/or alkoxyalkyl acetate of the formula (I)

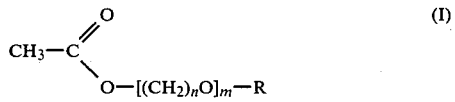

in which
 m is zero, 1 to 2, preferably zero or 1,
 n is 1 to 4, preferably 2 and
 R is ($C_1$–$C_5$)alkyl
in an aqueous phase containing a protective colloid and optionally a surface-active agent.

In accordance with the invention, the components for the manufacture of the isocyanate prepolymer mixture are chosen and tuned to one another in such a manner that the particles obtained have an optimum elasticity and that a sufficient reactivity of the isocyanate prepolymer mixture with water is ensured. Suitable isocyanate components are the known aliphatic, aromatic, cycloaliphatic or araliphatic di- or polyisocyanates, especially 2,4- and 2,6-toluylene diisocyanate, 2,4- and 2,6-hexahydrotoluylene diisocyanate, diphenylmethane-4,4'-diisocyanate, and higher homologs thereof, technical grade polymethylene-polyphenyl isocyanate (PAPI[R]), 1,4-tetramethylene diisocyanate and 1,6-hexamethylene diisocyanate. As di- or polyols there can be used the known aliphatic di- and polyols, the reaction products thereof with alkylene oxides such as ethylene oxide or propylene oxide, polyhydric alcohols and polyalkylene glycols, more particularly ethylene glycol, butylene glycols, 1,6-hexanediol, trimethylol propane, glycerol, hexanetriol, polyethylene and polypropylene glycols.

Especially good results are obtained, for example, with an isocyanate-prepolymer mixture obtained by reacting 2 to 3 mols of 1,2,6-hexanetriol and/or 1,1,1-trimethylol propane, 1 mol of 1,3-butanediol and 1 mol of propylene glycol 1,000 with 8 mols toluylene diisocyanate, the polyols being used in a distinct stoichiometric deficiency. A suitable solvent for the isocyanate prepolymer is especially a mixture of ethylene glycol acetate and xylene in a proportion by weight of 5:1 to 1:5.

The liquid organic phase immiscible with water to be used according to the invention generally contains the isocyanate-prepolymer mixture in an amount of from 10 to 40% by weight, preferably 12 to 30% by weight. Higher contents are also possible, for example up to 70% by weight. If the amounts of isocyanate-prepolymer are too small, the particles formed do not fully have the desired mechanical stability. Besides the isocyanate-prepolymer mixture and optionally the active substance to be encapsulated, the liquid organic phase immiscible with water contains from 2 to 85 and preferably 4 to 50% by weight of an alkyl and/or alkoxyalkyl acetate of formula (I). When alkyl acetates are used, their proportion by weight preferably exceed 10% by weight.

Suitable compounds of formula (I) are, for example: ethyl acetate, n- or i-propyl acetate, n- or i-butyl acetate, 2-ethoxyethyl acetate, 3-methoxy-n-butyl acetate or n-butyl-diglycol acetate, ethyl acetate and/or 2-ethoxyethyl acetate being preferred.

The balance up to 100% by weight of the liquid organic phase to be dispersed and immiscible with water consists of further solvents that are chemically inert to isocyanates, water and the active substance to be encapsulated, if any, for example aromatic or aliphatic hydrocarbons as well as esters, ethers and ketones, preferably toluene, xylenes, methylnaphthalenes, dimethylnaphthalenes, paraffin oils, cyclohexane, 4-methylcyclohexane, benzoic acid benzyl ester, diphenyl ether and isophorone.

The active substance to be encapsulated can be dispersed in the organic phase at a temperature above its melting point if it is not soluble in the solvent components of the organic phase or it can be added in dissolved form. The active substance, preferably a pesticide, but also a pharmaceutical agent, a disinfectant, a scenting substance or a perfume or any other chemical agent, which does not react with isocyanate or water, can be contained in the organic phase to be dispersed in an amount of from 0.1 to 80% by weight, preferably 1 to 60% and more preferably 5 to 40% by weight.

The aqueous phase contains 0.5 to 10% by weight of a protective colloid, preferably water-soluble or water-dispersible cellulose derivatives, for example carboxymethyl cellulose, hydroxylethyl cellulose or carboxymethyl-hydroxyethyl cellulse, polyvinyl alcohol and/or gum arabic. It is also possible to add non ionic, anionic or cationic surface-active substances in an amount of from 0.1 to 5% by weight. The amount added of the specified substances depends on the nature and composition of the organic phase to be dispersed, the molecular weight of the active substance to be encapsulated, the desired particle size, the reaction temperature and time, the time of stirring and the stirring speed and in each individual case it can be easily determined by a preliminary tests.

When practising the process of the invention, for example for encapsulating an active substance, the solution of the isocyanate-prepolymer mixture is first mixed with the active substance and the required additional solvents and the mixture obtained is added to the aqueous phase, preferably in a zone of high turbulence. To produce a zone of high turbulence common technical means are used, such as vessels with intense stirrer as well as tubular reactors with suitable stirring means. The mixture can be added either discontinuously or, when suitable equipment is used, also continuously. Series-connected homogenization devices may also be of advantage. The stirring time is from about 2 to 30 minutes, depending on the stirring device used and the reactivity of the prepolymer mixture. In this manner a dispersion of the organic phase in the aqueous phase is produced, in which the droplets formed have the desired size depending on the stirring intensity. In general, the diameter of the droplets is in the range of from 1 to 100 μm, preferably 5 to 20 μm. It is likewise possible to produce particles having a larger diameter of from 1 to 10 mm for special purposes. In the latter case the technical means have to be chosen accordingly.

The liquid organic phase to be dispersed can have a proportion of about 20 to 70% by volume relative to the total volume of the reaction mixture, a proportion of from 30 to 55% by volume being preferred.

The temperature of the encapsulation system can be kept constant during the entire process, but it is also possible to change the temperature after definite intervals. It is suitably in the range of from 0° to 95° C., preferably 20° to 60° C. A slight temperature increase towards the end of the reaction can be advantageous.

If it is desirable and suitable to adjust in the manufacturing process a definite pH, this could be done during or after the dispersion of the organic phase. This measure could be advantageous in those cases in which troubles could be expected by foam formation and a resulting increase in volume. The foam formation could be suppressed not only by adjusting the pH but also by adding antifoaming agents, for example triisobutyl phosphate, which could be advantageous in the case of acid active substance or active substances that react with bases.

It is surprising that the process of the invention yields homogeneous polyurethane-polyurea particles generally having a spherical shape, a smooth surface and filled in the interior with a textured mass formed by cross-linking reactions. This internal mass considerably improves the elasticity of the particles so that they have a high resistance to pressure not reached up to now and very favorable utilitarian properties and properties for specific use.

The internal structure of the particles produced according to the invention can be varied within wide limits depending on the manufacturing conditions (type of alkyl or alkoxyalkyl acetate). As shown by pictures taken in a scanning electron microscope or observed under the microscope, they can have the shape of gel- or jelly-like micellae in the range of molecular dispersion dimensions or the shape of a sponge or celluloar foam in the microscopic range. They may also have macroscopically visible pore structures. Preferred carriers, above all for plant protecting agents, are particles having the structure of a sponge or cellular foam in the microscopic range, as formed, for example with the use of 2-ethoxyethyl acetate and/or ethyl acetate (cf. Examples 1 to 8).

To measure the mechanical stability (especially the resistance to pressure) particles prepared according to Example 1 were used, having for practical reasons, diameters in the range of from 500 to 1,250 μm. In these measurements there was recorded the gradient of force with an increasing load of the particles under a plunger. With a loading speed of 1 mm per minute, the diameter of the area of contact plunger/particle corresponded to one half of the particle diameter in the unloaded state.

In all pressure deformation tests the forces possibly damaging the particles of the invention were above the limit of the measuring range of 40 N (N=Newton). As compared therewith, the capsules produced as described in Example 1 of DE-OS No. 1,519,853 broke on the average under average forces of 0.1 N only.

For the use of the particles according to the invention as carrier for plant protecting agents it is very important that none of the particle components has an undesired phytotoxic effect. Even after drying by known methods, preferably by spray drying, or also by the use of dehydrating agents, the particles carrying the pesticide can be well formulated. They can be applied without difficulty in the field. The textured internal mass of the particles ensures, inter alia, a slow release of the active substance and, hence, the depot effect thereof is improved.

The following examples illustrate the invention.

EXAMPLE 1

To prepare the aqueous phase 2 g of Mowiol$^{(R)}$4-88 (polyvinyl alcohol obtained by saponification of polyvinyl acetate, degree of saponification 87.7±1.0%; viscosity of a 4% aqueous solution 4±0.5 cP) and 2 g of Mowiol$^{(R)}$18-88 (polyvinyl alcohol obtained by saponification of polyvinyl acetate, degree of saponification 87.7±1.0%; viscosity of a 4% aqueous solution 18±1.5 cP) are dissolved in 100 g of water. To prepare the organic phase 50 g of dioctyl phthalate as substance to be encapsulated are mixed with 10 g of 2-ethoxyethyl acetate and to the mixture there are added 30 g of a 50% solution of a prepolymer obtained by reacting 8 mols of toluylene diisocyanate (ratio of isomers 2.4:2.6=80:20) with 1,2,6-hexanetriol, 1,3-butanediol and polypropylene glycol 1,000 in molar amounts of 3:1:1. As solvent for the prepolymer mixture a mixture of 2 ethoxyethyl acetate and xylene in a proportion by weight of 2:3 is used.

The organic phase is added slowly at 30° C. to the aqueous phase in a 500 ml reaction flask while vigorously stirring with an Ultra-Turrax$^{(R)}$ intense stirrer. The oil droplets are finely divided in the aqueous phase. The size of the droplets strongly depends on the shearing forces of the stirrer and is in the range of from about 1 μm to 20 μm. As soon as the desired particle size is reached, a weak movement of the reaction mixture is sufficient. After 30 minutes, the temperature is increased to 50° C. and the dispersion is kept at said temperature for 3 to 4 hours. While the outer skin of the particles forms at once, the inner structures form during the after-reaction. It proved advantageous to continue stirring of the dispersion formed for some hours at room temperature. The particles formed are isolated by spray drying the dispersion.

86 g of a freely flowing powder having an apparent density of 28.7 g and a compacted apparent density of 33.9 g per 100 ml containing encapsulated therein 57% by weight of dioctyl phthalate are obtained. The moisture content is about 0.3 to 0.8% by weight and the particles have a diameter in the range of from 1 to 20 μm.

EXAMPLE 2

The process is carried out as specified in Example 1 with the exception that, instead of the dioctylphthalate solution, a solution of 50 g of Heptenophos (7-chlorobicyclo[3,2,0]hepta-2,6-dien-6-yl-dimethyl phosphate) in 15 g of methylnaphthalene (industrial grade isomer mixture) is added to the organic phase.

By spray drying 90 g of a freely flowing powder having an apparent density of 36.5 and a compacted apparent density of 40.5 g per 100 ml and containing encapsulated therein 51% by weight of Heptenophos are obtained.

EXAMPLE 3

The aqueous phase is prepared as described in Example 1 from 2 g of Mowiol$^{(R)}$4–88 and 2 g of Mowiol$^{(R)}$18–88 in 80 g of water. The organic phase consists of 50 g of Heptenophos in 15 g of ethyl acetate and 40 g of a 50% solution of an isocyanate prepolymer according to Example 1.

As solvent for the isocyanate prepolymer ethyl acetate is used. The organic phase is added to the aqueous phase and the reaction mixture is worked up under the conditions specified in Example 1.

103 g of a freely flowing powder having an apparent density of 35.0 g and a compacted apparent density of 39.3 g per 100 ml and containing encapsulated therein 45% by weight of Heptenophos are obtained.

EXAMPLE 4

The aqueous phase is prepared from 2 g of Mowiol$^{(R)}$4–88 are 2 g of Mowiol$^{(R)}$18–88 in 80 g of water as described in Example 1. The organic phase consists of 40 g of Heptenophos in 25 g ethyl acetate and 40 g of a 50% solution of an isocyanate prepolymer prepared by reacting 8 mols of toluylene diisocyanate (proportion of isomers 2.4:2.6=80:20) with 5 mols of 1,2,6-hexanetriol. Ethyl acetate is used as solvent for the isocyanate prepolymer. The organic phase is added to the aqueous phase under the conditions specified in Example 1.

189 g of a finely disperse aqueous dispersion of microcapsules are obtained having a content of encapsulated Heptenophos of 21% by weight.

EXAMPLE 5

The aqueous phase is prepared under the conditions of Example 1 from 2.5 g of Mowiol$^{(R)}$18–88, 0.5 g of castor oil polyglycol ether with 40 ethylene oxide units as non ionic surface active substance and 100 g of water.

The organic phase consists of 30 g of Endosulfan (6,7,8,9,10-hexachloro-1,5-5a,9a-tetrahydro-6,9-methano-2,4,3-benzodioxathiepin-3-oxide) in 30 g of methylnaphthalene (industrial grade isomer mixture) and 45 g of a 50% solution of a prepolymer obtained by reacting 8 mols of toluylene diisocyanate (proportion of isomers 2.4:2.6=80:20) with 1,1,1-trimethylol propane, 1,3-butanediol and polypropylene glycol 1,000 in molar amounts of 3:1:1. As solvent a mixture of 2-ethoxyethyl acetate and xylene in a proportion by weight of 2:1 is used.

The organic phase is added to the aqueous phase under the conditions specified in Example 1.

208 g of a finely disperse aqueous dispersion of microcapsules is obtained containing 14% by weight of encapsulated Endosulfan.

EXAMPLE 6

The aqueous phase is prepared under the conditions of Example 1 from 2 g of Mowiol$^{(R)}$4–88 and 2 g of Mowiol$^{(R)}$18–88 in 80 g of water. The organic phase consists of 64 g of Dinoseb acetate (2-sec.butyl-4,6-dinitrophenyl acetate) in 10 g of 2-ethoxyethyl acetate and 40 g of a 50% solution of the prepolymer as used in Example 1. As solvent for the isocyanate prepolymer a mixture of 2-ethoxyethyl acetate and xylene in a proportion by weight of 2:3 is used. The organic phase is added to the aqueous phase and the reaction mixture is worked up under the conditions of Example 1.

105 g of a freely flowing powder are obtained having an apparent density of 41.6 g and a compacted apparent density of 51.4 g per 100 ml and containing encapsulatd therein 54% by weight of Dinoseb acetate.

EXAMPLE 7

In the manner described in Example 1 an aqueous phase is prepared from 4.5 g of Mowiol$^{(R)}$4–88 and 4.5 g of Mowiol$^{(R)}$18–88 in 200 g of water. The organic phase consists of 125 g of Pyrazophos (2-(0,0-diethyl-thionophosphory)5-methyl-6-carbethoxy-pyrazolo[1,5a]pyrimidine) and 2 g of epichlorhydrin in 50 g of xylene and 85 g of a 50% solution of the prepolymer mixture as used in Example 1. As solvent for the prepolymer mixture a mixture of 2-ethoxyethyl acetate and xylene in a proportion by weight of 2:3 is used. The organic phase is added to the aqueous phase under the conditions indicated in Example 1. After a reaction time of 4 to 5 hours at 50° C. and an after-reaction of 10 to 12 hours at room temperature, the particles are spray dried.

230 g of a freely flowing powder are obtained having an apparent density of 36 g and a compacted apparent density of 42.5 g per 100 ml and containing encapsulated therein 47% by weight of Pyrazophos.

EXAMPLE 8

An aqueous phase is prepared as described in Example 1 from 3 g gum arabic, 1.5 g Mowiol$^{(R)}$18–88 and 100 g of water. The organic phase consists of 125 g of Triazophos (0,0-diethyl(1-phenyl-1,2,4-triazol-3-yl)-thionophosphate) and 2 g of epichlorohydrin in 30 g of 2-ethoxyethyl acetate and 50 g of a 50% solution of the prepolymer mixture as used in Example 1, which is likewise dissolved in 2-ethoxyethyl acetate/xylene in a proportion by weight of 2:3. The organic phase is added to the aqueous phase under the conditions indicated in Example 1, the reaction time being the same.

311.5 g of a finely disperse aqueous dispersion of microcapsules is obtained containing 40% by weight of encapsulated Triazophos.

What is claimed is:
1. A process for the manufacture of pressure-resistance internally textured polyurethane-polyurea particles which comprises forming an organic solvent solution of isocyanate prepolymer which is a reaction product of a stoichiometric excess of an aliphatic, aromatic, cycloaliphatic or araliphatic di- or polyisocyanate with a diol or polyol, said reaction product having a mean molecular weight of from about 300 to 10,000, said organic solvent solution also containing from 2 to 85% by weight an alkyl and/or alkoxyalkyl acetate of the formula

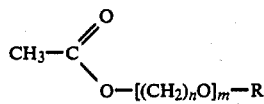

in which
m is 0 to 2
n is 1 to 4 and
R is $(C_1-C_5)$alkyl and dispersing said solvent solution as an organic phase at a temperature of 0° to 95° C. in an aqueous phase comprising water, a protective colloid and optionally a surface-active agent to form droplets of said organic phase wherein said isocyanate prepolymer reacts with the water of said aqueous phase to form said polyurethane-polyurea particles.

2. A process according to claim 1 wherein said organic phase contains an active substance to be encapsulated and said active substance is incorporated in said polyurethanepolyurea particles.

3. The process of claim 1, wherein 2-ethoxyethyl acetate and/or ethyl acetate is used as the alkoxyalkyl or alkyl and/or alkyl acetate.

4. The process of claim 1, wherein the organic phase contains 10 to 40% of isocyanate prepolymer.

5. The process of claim 1, wherein the isocyanate prepolymer is a reaction product of 2 to 3 mols of 1,2,6-hexanetriol and/or 1,1,1-trimethylol propane, 1 mol of 1,3-butanediol and 1 mol of polypropylene glycol 1,000 with 8 mols of toluylene diisocyanate.

6. The process of claim 2, wherein the organic phase contains from 0.1 to 80% by weight of active substance.

7. The process of claim 2, wherein the active substance is a pesticide.

8. The process of claim 1, wherein the aqueous phase contains 0.5 to 10% by weight of a cellulose derivative, polyvinyl alcohol and/or gum arabic as protective colloid.

9. The process of claim 7, wherein the aqueous phase contains 0.1 to 5% by weight of non ionic, anionic or cationic surface active substances.

10. The process of claim 1, wherein the organic phase is dispersed in the aqueous phase in a zone of high turbulence.

11. The process of claim 1, wherein the proportion of the organic phase amounts to 20 to 70% by volume, calculated on the total reaction volume.

12. The process of claim 1, wherein the organic phase is dispersed at a temperature of from 20° to 60° C.

13. The process of claim 1, wherein the droplets of the dispersed organic phase have a diameter of from 1 to 100 μm.

14. The process of claim 1, wherein the polyurethane-polyurea particles formed are isolated by spray drying.

* * * * *